US011727550B2

(12) United States Patent
Duval et al.

(10) Patent No.: US 11,727,550 B2
(45) Date of Patent: *Aug. 15, 2023

(54) IMAGE PROCESSING SYSTEMS AND METHODS OF USING THE SAME

(71) Applicant: Boston Scientific Scimed, Inc., Maple Grove, MN (US)

(72) Inventors: George Wilfred Duval, Sudbury, MA (US); Kirsten Viering, Newton, MA (US); Louis J. Barbato, Franklin, MA (US); Gang Hu, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,388

(22) Filed: Sep. 20, 2021

(65) Prior Publication Data
US 2022/0092753 A1 Mar. 24, 2022

Related U.S. Application Data

(60) Provisional application No. 63/081,420, filed on Sep. 22, 2020.

(51) Int. Cl.
*G06T 5/40* (2006.01)
*A61B 1/05* (2006.01)
(Continued)

(52) U.S. Cl.
CPC ................. *G06T 5/40* (2013.01); *A61B 1/05* (2013.01); *A61B 1/0676* (2013.01); *G06T 3/40* (2013.01);
(Continued)

(58) Field of Classification Search
CPC .... G06T 5/40; G06T 3/40; G06T 5/50; G06T 2207/10016; G06T 2207/10068;
(Continued)

(56) References Cited

U.S. PATENT DOCUMENTS 9,947,085 B2    4/2018  St. Romain, II et al.
2010/0278423 A1*  11/2010  Itoh ......................... G06T 5/008
                                                      382/274

(Continued)

OTHER PUBLICATIONS

Anonymous: "Adaptive histogram equalization—Wikipedia", Feb. 6, 2014 (Feb. 6, 2014), XP055484979, Retrieved from the Internet: URL:https://en.wikipedia.org/w/index.php?title=Adaptive_histogram_equalization&oldid=594245673 [retrieved on Jun. 15, 2018] p. 2-p. 3.

(Continued)

*Primary Examiner* — Sunghyoun Park
(74) *Attorney, Agent, or Firm* — Bookoff McAndrews, PLLC

(57) ABSTRACT

A method is provided for enhancing video images in a medical device. The method includes receiving a first image frame and a second image frame from an image sensor. First image sub-blocks are generated by dividing the first image frame. Second image sub-blocks are generated by dividing the second image frame based on the first image sub-blocks. Histogram data of the first image sub-blocks is generated. Histogram data of the second image sub-blocks is generated based on the histogram data of the first image sub-blocks. A histogram enhanced image frame is generated based on the histogram data of the second image sub-blocks. A video image stream is generated based on the histogram enhanced image frame.

20 Claims, 5 Drawing Sheets

(51) Int. Cl.
  *A61B 1/06* (2006.01)
  *G06T 3/40* (2006.01)
  *G06T 5/50* (2006.01)
  *H04N 23/56* (2023.01)
  *H04N 23/80* (2023.01)
  *H04N 23/50* (2023.01)

(52) U.S. Cl.
  CPC ............... *G06T 5/50* (2013.01); *H04N 23/56* (2023.01); *H04N 23/80* (2023.01); *G06T 2207/10016* (2013.01); *G06T 2207/10068* (2013.01); *G06T 2207/20021* (2013.01); *H04N 23/555* (2023.01)

(58) Field of Classification Search
  CPC ............ G06T 2207/20021; A61B 1/05; A61B 1/0676; H04N 5/2256; H04N 5/23229; H04N 2005/2255
  See application file for complete search history.

(56) References Cited

U.S. PATENT DOCUMENTS

| | | | |
|---|---|---|---|
| 2012/0275658 A1* | 11/2012 | Hurley | G06T 7/11 382/109 |
| 2014/0334667 A1* | 11/2014 | Eswara | G06V 20/13 382/103 |
| 2016/0328831 A1* | 11/2016 | St. Romain, II | G06T 5/008 |
| 2016/0335751 A1* | 11/2016 | Sidar | H04N 9/646 |
| 2017/0301095 A1* | 10/2017 | Zhang | G06T 7/11 |

OTHER PUBLICATIONS

International Search Report issued in International Application No. PCT/US2021/051074 dated Jan. 4, 2022 (15 pages).
Kentaro Kokufuta et al: "Real-Time Processing of Contrast Limited Adaptive Histogram Equalization on FPGA", 2010 International Conference on Field Programmable Logic and Applications (FPL), IEEE, Piscataway, NJ, USA, Aug. 31, 2010 (Aug. 31, 2010), pp. 155-158, XP031854493, ISBN 978-1-4244-7842-2 abstract p. 15 7, left column.; figures 1,3.

* cited by examiner

IMAGE PROCESSING SYSTEMS AND METHODS OF USING THE SAME

CROSS-REFERENCE TO RELATED APPLICATIONS

This application claims the benefit of priority from U.S. Provisional Application No. 63/081,420, filed on Sep. 22, 2020, which is incorporated by reference herein in its entirety.

TECHNICAL FIELD

Various aspects of the disclosure relate generally to image processing systems, devices, and related methods. Examples of the disclosure relate to systems, devices, and related methods for enhancing video images, among other aspects.

BACKGROUND

Technological developments have given users of medical systems, devices, and methods, the ability to conduct increasingly complex medical procedures on various patients. However, in the field of minimally invasive surgeries, accurately visualizing target treatment sites within a patient, for example, tumors or lesions located in a gastrointestinal tract of the patient, is a known challenge. Although image enhancement techniques using histogram enhancement methods improve image quality, highly iterative processes required for histogram enhancements may overburden the image processors, cause image processing delays, and/or limit its effectiveness for video images.

SUMMARY

Aspects of the disclosure relate to, among other things, systems, devices, and methods for providing an image processing system and sub-block generation logic, histogram enhancement logic, and mapping/interpolation logic, among other aspects. Each of the aspects disclosed herein may include one or more of the features described in connection with any of the other disclosed aspects.

According to one aspect, a method is provided for enhancing video images in a medical device. The method includes receiving a first image frame and a second image frame from an image sensor. First image sub-blocks are generated by dividing the first image frame. Second image sub-blocks are generated by dividing the second image frame based on the first image sub-blocks. Histogram data of the first image sub-blocks is generated. Histogram data of the second image sub-blocks is generated based on the histogram data of the first image sub-blocks. A histogram enhanced image frame is generated based on the histogram data of the second image sub-blocks. A video image stream is generated based on the histogram enhanced image frame.

Any of the methods described herein may include any of the following steps. One or more iterations of sizing each of the first image sub-blocks is performed. A size of each of the first image sub-blocks based on the one or more iterations of the first image sub-blocks is determined. A size of each of the second image sub-blocks is determined based on one or more iterations of sizing each of the second image sub-blocks and/or a size of each of the first image sub-blocks. The histogram data of the first image sub-blocks is generated by generating a histogram for each of the first image sub-blocks, and determining a clipping level of each histogram of the first image sub-blocks. The clipping level of each histogram of the first image sub-blocks is determined based on one or more iterations of clipping each histogram of the first image sub-blocks. The histogram data of the second image sub-blocks is generated by generating a histogram for each of the second image sub-blocks, and determining a clipping level of each histogram of the second image sub-blocks. The histogram for each of the second image sub-blocks is generated at least based on a cumulative distribution function. The clipping level of each histogram of the second image sub-blocks is determined based on one or more iterations of clipping each histogram of the second image sub-blocks and/or a clipping level of each histogram of the first image sub-blocks. The histogram data of the second image sub-blocks is generated by distributing clipped data of each histogram of the second image sub-blocks to the histogram for each of the second image sub-blocks. The histogram enhanced image frame generated by interpolating the histogram data of the second image sub-blocks. A plurality of image frames is received from the image sensor. Sub-blocks in each of the plurality of image frames is generated. The plurality of image frames is at least three frames. A histogram for each sub-block of the plurality of image frames is generated. A clipping level of each sub-block of the plurality of image frames is determined based on an average histogram data of the plurality of image frames. The histogram data of the second image sub-blocks is generated by generating a histogram for each of the second image sub-blocks, and determining a clipping level of each histogram of the second image sub-blocks. The clipping level of each histogram of the second image sub-blocks is determined based on one or more iterations of clipping each histogram of the second image sub-blocks and/or an average histogram data of the plurality of image frames.

According to one aspect, a medical device includes a shaft, an image sensor coupled to a distal end of the shaft, and at least one illumination device coupled to the distal end of the shaft. The medical device further includes one or more computer readable media storing instructions performing image processing to enhance video images and one or more processors configured to execute the instructions to perform the image processing. The one or more processors receive a first image frame and a second image frame from the image sensor. The one or more processors generate first image sub-blocks by dividing the first image frame. The one or more processors generate second image sub-blocks of the second image frame based on the first image sub-blocks. The one or more processors generate histogram data of the first image sub-blocks. The one or more processors generate histogram data of the second image sub-blocks based on the histogram data of the first image sub-blocks. The one or more processors generate a histogram enhanced image frame based on the histogram data of the second image sub-blocks. The one or more processors generate a video image stream based on the histogram enhanced image frame.

Any of the medical device described herein may include any of the following features. The one or more processors generate the second image sub-blocks by determining a size of each of the second image sub-blocks based on one or more iterations of sizing each of the second image sub-blocks and/or a size of each of the first image sub-blocks. The one or more processors generate the histogram data of the second image sub-blocks comprises. The one or more processors determine a clipping level of each histogram of the second image sub-blocks is based on one or more iterations of clipping each histogram of the second image sub-blocks and/or a clipping level of each histogram of the first image sub-blocks. The one or more processors generate the histogram data of the second image sub-blocks by determining wherein a clipping level of each histogram of the second image sub-blocks is based on one or more iterations of clipping each histogram of the second image sub-blocks and/or an average histogram data of a plurality of image frames.

According to one aspect, a non-transitory computer-readable medium stores instructions for enhancing video images. The instructions, when executed by one or more processors, causes the one or more processors to perform operations. The one or more processors receive a first image frame and a second image frame from an image sensor. The one or more processors generate first image sub-blocks by dividing the first image frame. The one or more processors generate second image sub-blocks of the second image frame based on the first image sub-blocks. The one or more processors generate histogram data of the first image sub-blocks. The one or more processors generate histogram data of the second image sub-blocks based on the histogram data of the first image sub-blocks. The one or more processors generate a histogram enhanced image frame based on the histogram data of the second image sub-blocks. The one or more processors generate a video image stream based on the histogram enhanced image frame.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
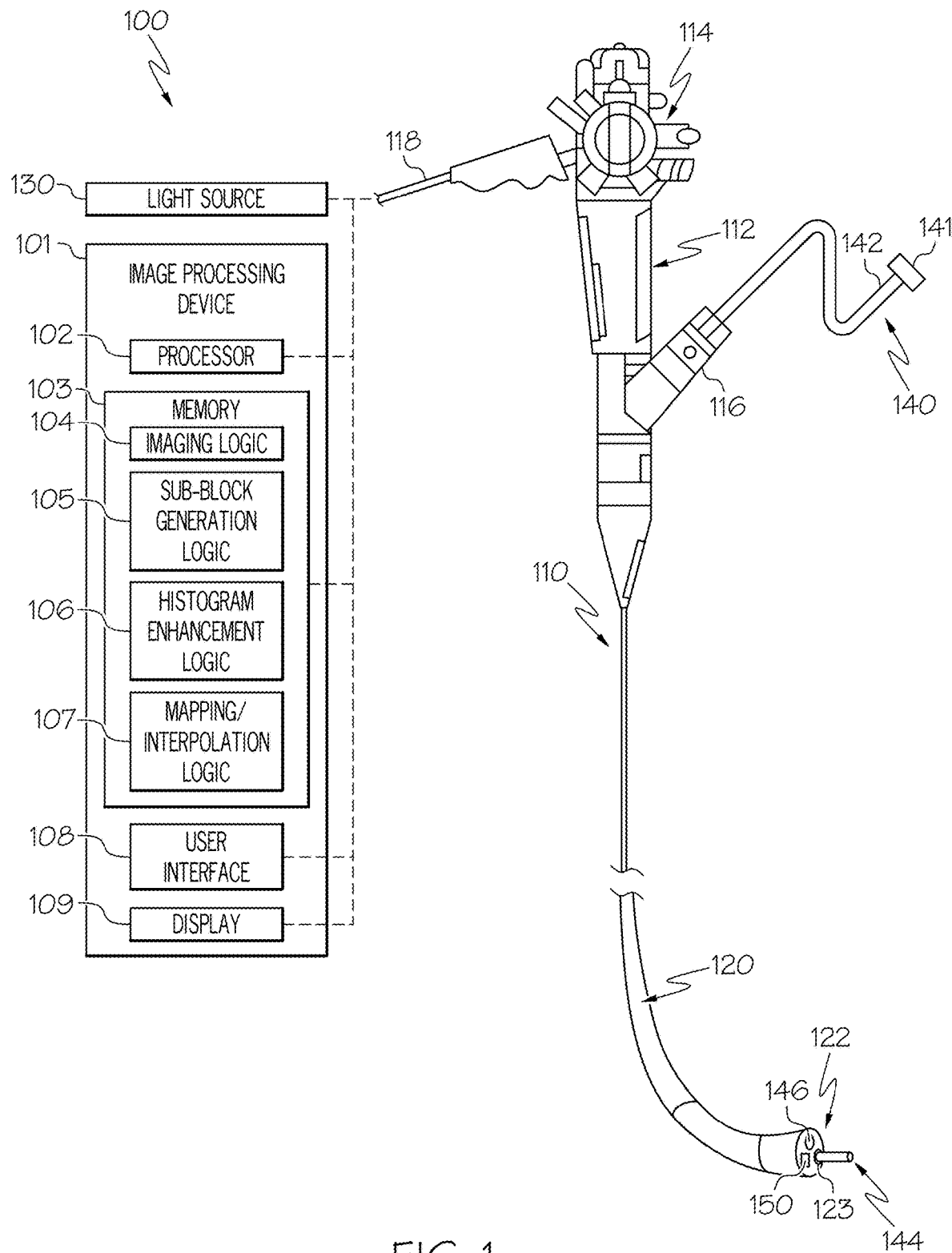
FIG. 1 is a schematic view of an exemplary medical system, according to aspects of this disclosure.

Examples of the disclosure include systems, devices, and methods for enhancing video images of one or more treatment sites within a subject (e.g., patient) using image contrast enhancement techniques. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to capture video image frames of one or more treatment/diagnostic sites within a subject using one or more image sensors of a medical system. In some embodiments, a medical device may include an image processing device including a processor and a memory storing one or more executable instructions and algorithms for enhancing video image frames of one or more treatment/diagnostic sites of a patient. Further, the processor and the memory may generate contrast enhanced image frames using histogram enhancement techniques. In embodiments, the memory may include programmable and executable instructions in accordance with an imaging logic, a sub-block generation logic, a histogram enhancement logic, and a mapping/interpolation logic. Further, the image processing device may include a user interface operable to receive a user input thereon. The processed image produced by the image processing device of the medical device may include enhanced video image frames with pixel values that may be outputted to a display device.

Examples of the disclosure may relate to systems, devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices, or sterilizable, reusable devices. Reference will now be made in detail to examples of the disclosure described above and illustrated in the accompanying drawings. Wherever possible, the same reference numbers will be used throughout the drawings to refer to the same or like parts.

FIG. 1 shows a schematic depiction of an exemplary medical system 100 in accordance with an example of this disclosure. The medical system 100 may include one or more light sources 130, an image processing device 101, a medical instrument 110, and a medical device 140. The image processing device 101 may be communicatively coupled to the medical instrument 110 by, for example, a wired connection 118, a wireless connection, and the like. In examples, the image processing device 101 is a computer system incorporating a plurality of hardware components that allow the image processing device 101 to receive data (e.g., image sensor data), process information (e.g., intensity, motion, or spectral data and the like), and/or generate a processed image or a video image stream for outputting to a user of the medical system 100. Illustrative hardware components of the image processing device 101 may include at least one processor 102, at least one memory 103, at least one user interface 108, and at least one display 109.

The processor 102 of the image processing device 101 may include any computing device capable of executing machine-readable instructions, which may be stored on a non-transitory computer-readable medium, for example, the memory 103 of the image processing device 101. By way of example, the processor 102 may include a controller, an integrated circuit, a microchip, a computer, and/or any other computer processing unit operable to perform calculations and logic operations required to execute a program. As described in greater detail herein, the processor 102 is configured to perform one or more operations in accordance with the instructions stored on the memory 103.

Still referring to FIG. 1, the memory 103 of the image processing device 101 may include a non-transitory computer readable medium that stores machine-readable instructions thereon, for example, an imaging logic 104, a sub-block generation logic 105, a histogram enhancement logic 106, and a mapping/interpolation logic 107. The imaging logic 104 may include executable instructions or algorithms that allow the medical system 100 to capture digital images (e.g., raw digital images) by activating one or more components of the medical instrument 110, for example, one or more image sensors 150 and one or more light sources 130. The one or more image sensors 150 may include, for example, one or more color image sensors and/or monochromatic image sensors. The one or more light sources 130 may be configured to emit white light, color light (e.g., red, blue, and green), ultraviolet light, near-infrared (NIR) light, and/or various other wavelengths within or beyond a visible spectrum. The one or more light sources 130 may be one or more light-emitting diodes (hereinafter LEDs). Further, the image sensor 150 (or one or more image sensors) of the medical instrument 110 may be communicatively coupled to the image processing device 101 of the medical system 100, for example, via the wired connection 118, a wireless connection, and/or the like. The image sensor 150 of the medical instrument 110 may be configured and operable to capture a raw image (e.g., a digital image) of a surrounding environment of the tip 122 of the shaft 120.

In one embodiment, the image sensor 150 may include a photosensor array (not shown) that may be configured and operable to convert a light beam received by the photosensor array into an electrical current. For example, the electrical current may be generated by the photosensor array arranged on the image sensor 150 when photons from the received light are absorbed by a plurality of photosites (not shown) arranged on the photosensor array. Further, each of the plurality of photosites may be operable to receive, capture, and absorb different wavelengths of the incoming light at a location of the photosites along a surface of the photosensor array. Accordingly, the plurality of photosites may capture the incoming light and may generate an electrical signal which is quantified and stored as a numerical value in a resulting processed image file. It should be appreciated that the photosensor array may include various suitable shapes, sizes, and/or configurations.

In some embodiments, the memory 103 (e.g., imaging logic 104, sub-block generation logic 105, histogram enhancement logic 106, and mapping/interpolation logic 107) of the image processing device 101 may include a contrast limited adaptive histogram equalization (CLAHE) algorithm in order to enhance video image frames. CLAHE is an image processing algorithm to intensify the contrast of both luminance and color in image regions where differences between neighboring pixels are small. As a result, fine details that are enhanced may be better detected and diagnosed by a physician. In embodiments, the medical instrument 110 (e.g., an endoscope) using CLAHE may provide enhanced images of polyps or blood vessels on an intestine wall. In embodiments, these images are real-time video image frames captured by the image sensor(s) 150 of the medical instrument 110.

Still referring to FIG. 1, the sub-block generation logic 105 may include executable instructions or algorithms (e.g., CLAHE) that allow the medical system 100 to, for example, generate a plurality of sub-blocks (or tiles) by dividing one or more image frames captured by the image sensor 150. In one embodiment, the sub-block generation logic 105 may perform one or more iterations to determine a best fit size for each of the plurality of sub-blocks. The histogram enhancement logic 106 may include executable instruction or algorithms (e.g., CLAHE) that allow the medical system 100 to, for example, generate one or more histograms for each of the plurality of sub-blocks generated by the sub-block generation logic 105. The histogram enhancement logic 106 may also determine one or more clipping threshold levels to clip the one or more histograms generated for each of the plurality of sub-blocks in order to enhance various features in the one or more image frames. In one embodiment, the histogram enhancement logic 106 may perform one or more iterations to determine a best clipping threshold level for enhancing the one or more image frames without distorting the images. The mapping/interpolation logic 107 may include executable instructions or algorithms (e.g., CLAHE) that allow the medical system 100 to, for example, map the histogram enhanced images and perform interpolation to render enhanced image frames in order to generate a video image stream.

In some embodiments, the imaging logic 104, the sub-block generation logic 105, the histogram enhancement logic 106, and/or the mapping/interpolation logic 107 may include executable instructions and algorithms that allow the medical system 100 to execute periodic image processing of a target site automatically without requiring user input. In other embodiments, the image processing device 101 may be configured to receive user inputs to initiate image processing of a target site, for example, from a user interface 108 of the image processing device 101. It should be appreciated that, in some embodiments, the user interface 108 may be a device integral with the image processing device 101, and in other embodiments, the user interface 108 may be a remote device in communication (e.g., wireless, wired, etc.) with the image processing device 101, including switches, buttons, or other inputs on the medical instrument 110.

It should be understood that various programming algorithms and data that support an operation of the medical system 100 may reside in whole or in part in the memory 103. The memory 103 may include any type of computer readable medium suitable for storing data and algorithms, such as, for example, random access memory (RAM), read only memory (ROM), a flash memory, a hard drive, and/or any device capable of storing machine-readable instructions. The memory 103 may include one or more data sets, including, but not limited to, image data from one or more components of the medical system 100 (e.g., the medical instrument 110, the medical device 140, etc.).

Still referring to FIG. 1, the medical instrument 110 may be configured to facilitate positioning of one or more components of the medical system 100 relative to a subject (e.g., a patient), such as, for example, the medical device 140. In some embodiments, the medical instrument 110 may be any type of endoscope, duodenoscope, gastroscope, colonoscope, ureteroscope, bronchoscope, catheter, or other delivery system, and may include a handle 112, an actuation mechanism 114, at least one port 116, and a shaft 120. The handle 112 of the medical instrument 110 may have one or more lumens (not shown) that communicate with a lumen(s) of one or more other components of the medical system 100. The handle 112 further includes the at least one port 116 that opens into the one or more lumens of the handle 112. As described in further detail herein, the at least one port 116 is sized and shaped to receive one or more instruments therethrough, such as, for example, the medical device 140 of the medical system 100.

The shaft 120 of the medical instrument 110 may include a tube that is sufficiently flexible such that the shaft 120 is configured to selectively bend, rotate, and/or twist when being inserted into and/or through a subject's tortuous anatomy to a target treatment site. The shaft 120 may have one or more lumens (not shown) extending therethrough that include, for example, a working lumen for receiving instruments (e.g., the medical device 140). In other examples, the shaft 120 may include additional lumens such as a control wire lumen for receiving one or more control wires for actuating one or more distal parts/tools (e.g., an articulation joint, an elevator, etc.), a fluid lumen for delivering a fluid, an illumination lumen for receiving at least a portion of an illumination assembly (not shown), and/or an imaging lumen for receiving at least a portion of an imaging assembly (not shown).

Still referring to FIG. 1, the medical instrument 110 may further include a tip 122 at a distal end of the shaft 120. In some embodiments, the tip 122 may be attached to the distal end of the shaft 120, while in other embodiments the tip 122 may be integral with the shaft 120. For example, the tip 122 may include a cap configured to receive the distal end of the shaft 120 therein. The tip 122 may include one or more openings that are in communication with the one or more lumens of the shaft 120. For example, the tip 122 may include a working opening 123 through which the medical device 140 may exit from a working lumen of the shaft 120. It should be appreciated that other one or more openings at the tip 122 of the shaft 120 are not shown. The actuation mechanism 114 of the medical instrument 110 is positioned on the handle 112 and may include knobs, buttons, levers, switches, and/or other suitable actuators. The actuation mechanism 114 is configured to control at least a deflection of the shaft 120 (e.g., through actuation of a control wire).

The medical device 140 of the medical system 100 may include a catheter having a longitudinal body 142 between a proximal end 141 of the medical device 140 and a distal end 144 of the medical device 140. The longitudinal body 142 of the medical device 140 may be flexible such that the medical device 140 is configured to bend, rotate, and/or twist when being inserted into a working lumen of the medical instrument 110. The medical device 140 may include a handle at the proximal end 141 of the longitudinal body 142 that may be configured to move, rotate, and/or bend the longitudinal body 142. Further, the handle at the proximal end 141 of the medical device 140 may define one or more ports (not shown) sized to receive one or more tools through the longitudinal body 142 of the medical device 140.

Still referring to FIG. 1, the medical instrument 110 may be configured to receive the medical device 140 via the at least one port 116, through the shaft 120 via a working lumen, and to the working opening 123 at the tip 122. In this instance, the medical device 140 may extend distally out of the working opening 123 and into a surrounding environment of the tip 122, such as, for example, at a target treatment site of a subject as described in further detail below. The distal end 144 of the medical device 140 may extend distally from the tip 122 in response to a translation of the longitudinal body 142 through the working lumen of the shaft 120. The medical device 140 may include one or more end effectors (not shown) at the distal end 144 of the longitudinal body 142, for performing one or more operations at a target treatment site.

In one embodiment, the medical instrument 110 may be further configured to receive the one or more light sources 130 through the shaft 120 via at least one of the lumens of the medical instrument 110 for connection to an optical fiber 146. In the example, the one or more light sources 130 are shown as a separate component from the image processing device 101 such that the light sources 130 are coupled to the medical instrument 110 separately from the image processing device (e.g., via a cable). It should be appreciated that, in other embodiments, the one or more light sources 130 may be included on the image processing device 101 such that the light sources 130 may be communicatively coupled to the medical instrument 110 with the image processing device 101.

Still referring to FIG. 1, the tip 122 of the medical instrument 110 may include the optical fiber 146 and the image sensor 150 at the tip 122. In one embodiment, the optical fiber 146 may be coupled to the one or more light sources 130 of the medical system 100, such that each of the one or more light sources 130 may transmit light through the single, optical fiber 146. Although not shown, it should be appreciated that multiple light sources 130 may be coupled to the optical fiber 146 via a fiber splitter/combiner. The optical fiber 146 of the medical instrument 110 may be configured and operable to deliver various amplitudes of light, from the one or more light sources 130, distally from the tip 122 of the shaft 120. In some embodiments, the optical fiber 146 may be configured to deliver white light, ultraviolet light, near-infrared (NIR) light, and/or various other wavelengths within or beyond a visible spectrum.

In other embodiments, the medical instrument 110 may include, although not shown, a multicolor LED assembly at the tip 122 of the shaft 120. The multicolor LED assembly may, for example, include one or more LEDs disposed in an annular array about the image sensor 150. Each of the LEDs may be configured and operable to transmit a different light wavelength and/or amplitude relative to one another. It should be understood that different illumination sources may generate different spectra (e.g., red, green, and blue colors).

In other embodiments, as further described herein, the image sensor 150 may be configured and operable to fully capture all incoming light at each individual pixel location of the image sensor 150 irrespective of a color of the incoming light.

Still referring to FIG. 1, the medical instrument 110 of the medical system 100 may be inserted within a subject's body (not shown) to position the tip 122 adjacent to a target site. For example, the shaft 120 may be guided through a digestive tract of a subject (e.g., patient) by inserting the tip 122 into a nose or mouth (or other suitable natural body orifice) of the subject's body and traversed through a gastrointestinal tract of the subject's body (e.g., an esophagus, a stomach, a small intestine, etc.) until reaching the target site. It should be appreciated that a length of the shaft 120 may be sufficient so that a proximal end of the medical instrument 110 (including the handle 112) is external of the subject, while the tip 122 of the medical instrument 110 is internal to the subject's body. While this disclosure relates to the use of the medical system 100 in a digestive tract of a subject, it should be understood that the features of this disclosure could be used in various other locations (e.g., other organs, tissue, etc.) within a subject's body.

Figure 2:
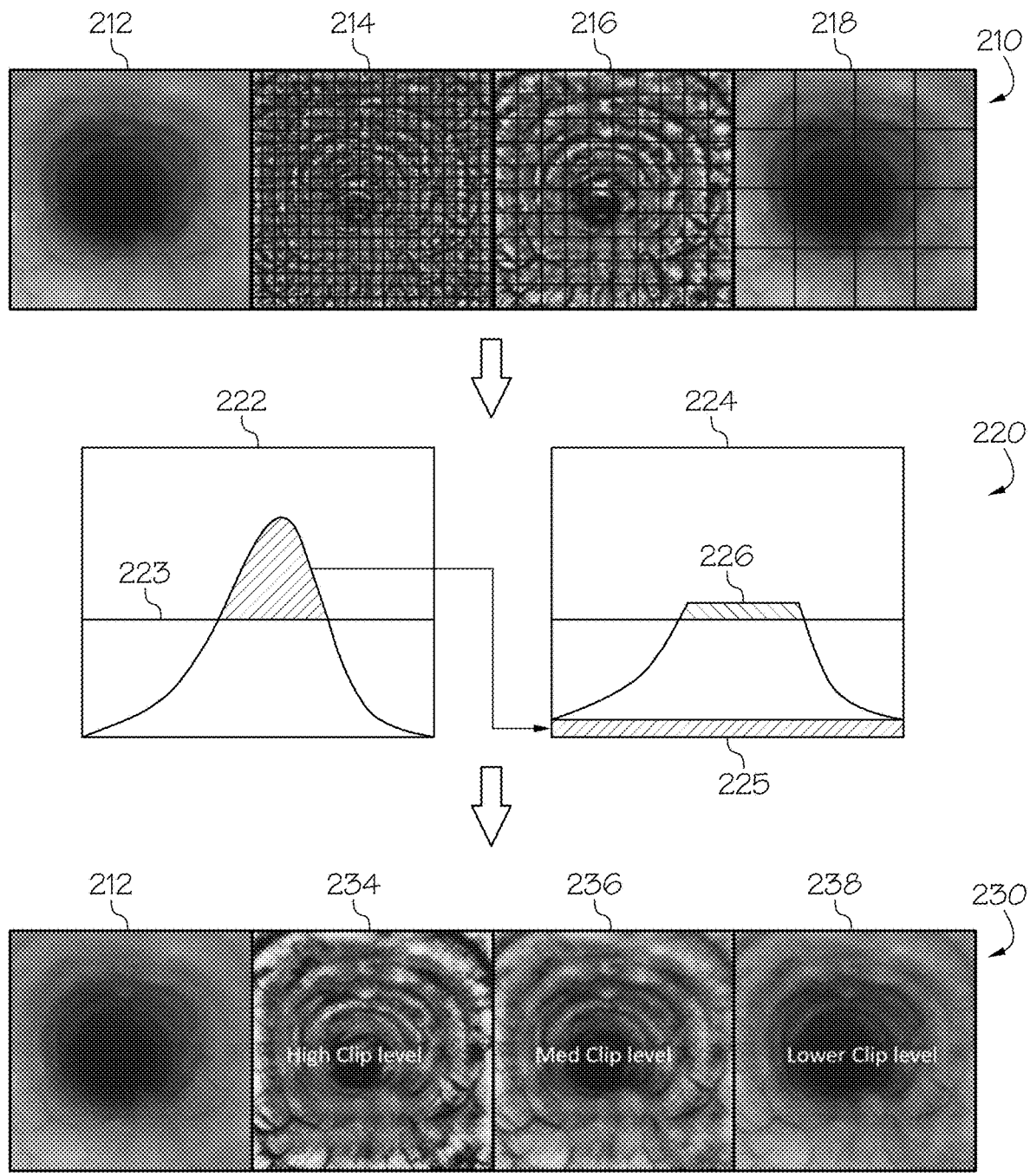
FIG. 2 illustrates an exemplary process of enhancing an image frame using the medical system of FIG. 1, according to aspects of this disclosure.

FIG. 2 shows an exemplary image enhancement process utilizing histogram enhancement algorithms (e.g., CLAHE) to generate a contrast enhanced video image stream in accordance with embodiments of this disclosure. In one exemplary embodiment of FIG. 2, at step 210, the image sensor 150 may capture an image frame(s) (e.g., a raw digital image frame) 212 at a target site (e.g., an esophagus, a stomach, a small intestine, other organs, tissue, polyp, etc.)

of a subject (e.g., patient) that may be illuminated by the light source 130 (or the multicolor LED assembly) at the tip 122 of the shaft 120. The sub-block generation logic 105 may then determine the number and/or size of sub-blocks of the image frame 212. For example, when the sub-block generation logic 105 receives the image frame 212, the sub-block generation logic 105 may divide the image frame 212 into a plurality of sub-blocks (e.g., 214, 216, or 218). The sub-block generation logic 105 may perform one or more iterations to determine the ideal sub-block size to emphasize and enhance one or more features in the image frame 212. The enhancement of the one or more features in the image frame 212 may improve, for example, a low light image by providing higher contrast. That is, the improved features in the image frame 212 may provide better visual depth in a lumen and/or better definition in vascularity structure of the walls of an intestine while guiding the medical instrument 110 in the target site for diagnostics and/or applied therapies.

Still referring to step 210 of FIG. 2, the sub-block generation logic 105 may divide the image frame 212 into a first set of sub-blocks (or first sub-block matrix) 214. In one example, the size of the sub-blocks in the first set of sub-blocks 214 may be too small for enhancing the vascularity features and/or improving depth of the lumen in the image frame 212. That is, too small of sub-blocks (e.g., first set of sub-blocks 214) in the image frame 212 may create unwanted over-enhancements with additional ridges that may distort the overall lumen by taking away the vascularity depth. The sub-block generation logic 105 may then divide the image frame 212 into a second set of sub-blocks (or second sub-block matrix) 216, which may be slightly larger than the first set of sub-blocks 214. In this example, the slightly larger second set of sub-blocks 216 may provide less emphasis in, for example, homogenous regions of the image frame 212. However, the second set of sub-blocks 216 may still be insufficient to interpret the vascular structures over the emphasized ridges of the image frame 212 in the second set of sub-blocks 216. The sub-block generation logic 105 may then divide the image frame 212 into a third set of sub-blocks (or third sub-block matrix) 218. The third set of sub-blocks 218 may be larger than the second set of sub-blocks 216. The third set of sub-blocks 218 may have a sub-block size, for example, that is just below the size of the largest feature in the image frame 212. In this embodiment, the size of the third set of sub-blocks 218 may provide the best balance in the regions having homogenous regions, and other regions with enough definition to draw more definition in the image frame 212 without causing too much over-enhancements. The sub-block generation logic 105 may perform multiple iterations for dividing the image frame 212 into sub-blocks with a suitable size. The image frame 212 may be divided into sub-blocks based on the homogeneity of the features in the image frame 212. That is, the sub-generation logic 105 may determine the suitable size of the sub-blocks of image frame 212 based on significant changes in the quantity of color and/or intensity of the features in the image frame 212.

Still referring to FIG. 2, at step 220, the histogram enhancement logic 106 may generate one or more histograms for each of the sub-blocks (e.g., third set of sub-blocks 218) that were generated by the sub-block generation logic 105 in step 210. For example, the histogram enhancement logic 106 may determine intensity levels of the pixels in each sub-block of the third set of sub-blocks 218 and generate a histogram 222 based on the frequency of intensity levels determined in each sub-block of the third set of sub-blocks 218. The histogram enhancement logic 106 may then derive a cumulative distribution function (CDF) of the histogram 222 in order to equalize the histogram 222 and redistribute the pixel intensity levels based on the CDF of the histogram 222. In some embodiments, equalizing the histogram 222 may over-amplify the contrast levels in highly concentrated pixel intensity regions, which may cause noise to be amplified. As such, the histogram enhancement logic 106 may limit the over-amplification of contrast levels by clipping the histogram 222 at a clipping threshold level 223. In one embodiment, the histogram enhancement logic 106 may generate a clipped histogram 224 by clipping the histogram 222 at the clipping threshold level 223. For example, the histogram enhancement logic 106 may redistribute the intensity values above the clipping threshold level 223 of the histogram 222 into a bottom portion 225 of the clipped histogram 224. The redistribution of the intensity values above the clipping threshold level 223 may result in excess intensity values 226. However, the redistribution of the intensity values may be repeated until the excess intensity values 226 become negligible.

Still referring to FIG. 2, at step 230, the histogram enhancement logic 106 may perform one or more iterations to determine the clipping threshold level 223 of the sub-blocks (e.g., third set of sub-blocks 218) of the image frame 212. Similar to the sub-block size determination process described in step 210, the histogram enhancement logic 106 may first determine a first clipping threshold level 234. As shown in FIG. 2, the first clipping threshold level 234 may be a high clipping threshold level that may create unwanted over-enhancements with additional ridges that may distort the overall lumen by taking away the vascularity depth. The histogram enhancement logic 106 may then determine a second clipping threshold level 236 that may be lower than the first clipping threshold level 234. In this example, the lower second clipping threshold level 236 may provide less emphasis in the homogenous regions of the image frame 212. However, the second clipping threshold level 236 may still be insufficient to interpret the vascular structures over the emphasized ridges of the image frame 212. The histogram enhancement logic 106 may then determine a third clipping threshold level 238 that may be lower than the second clipping threshold level 236. The third clipping threshold level 238 may provide sufficient definition improvement without distorting the image. The histogram enhancement logic 106 may perform multiple iterations for determining a suitable clipping threshold level.

Figure 3:
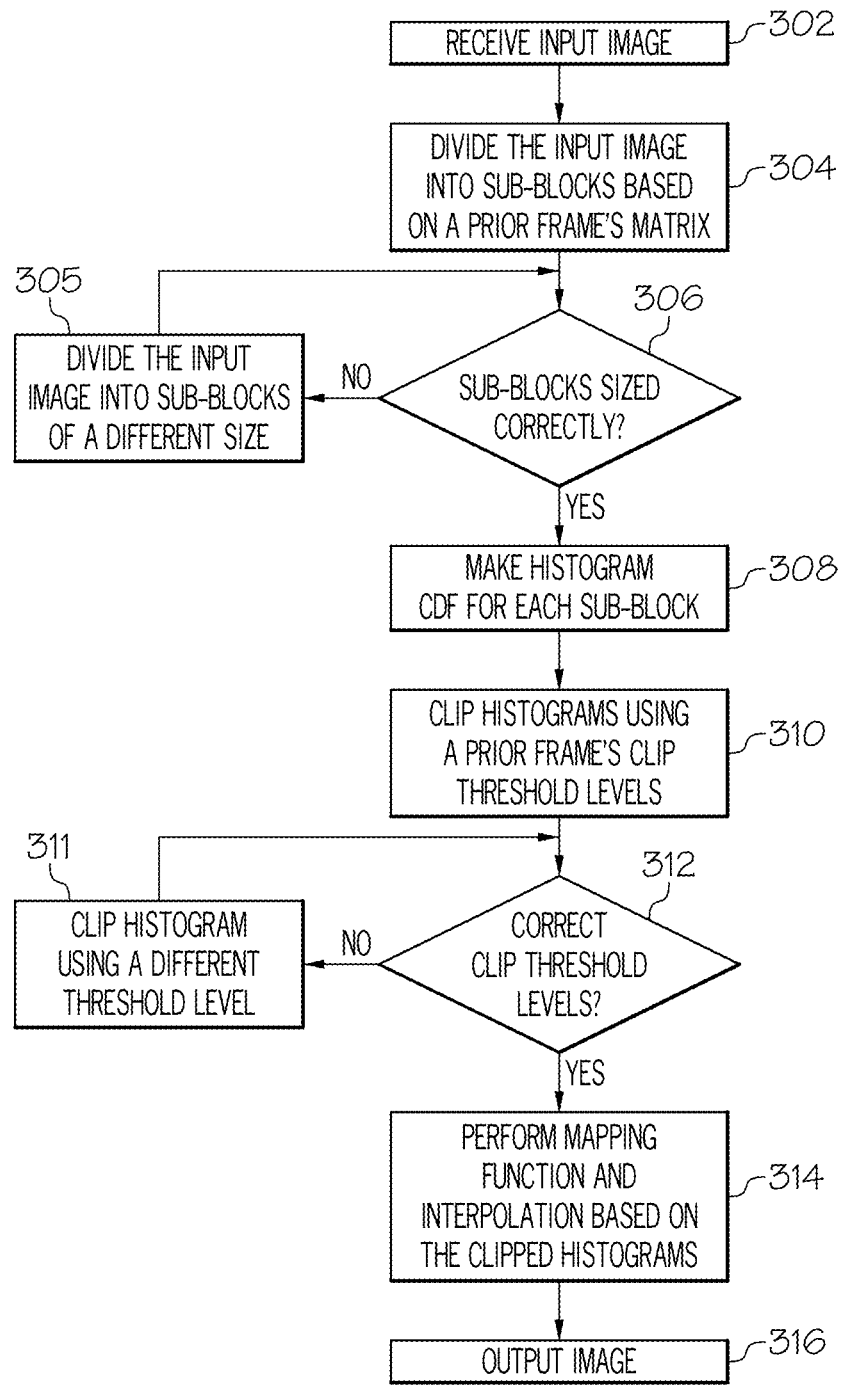
FIG. 3 illustrates an exemplary process of enhancing video images using the medical system of FIG. 1, according to aspects of this disclosure.

In some embodiments, the processes for determining the sub-blocks (e.g., third set of sub-blocks 218) and the clipping threshold level (e.g., third clipping threshold level 238) for the image frame 212 at steps 210 and 230 may require many iterations. Thus, enhancing each image frame in a video image stream with numerous iterations may cause unacceptable delays for generating enhanced real-time video image streams. FIG. 3 shows an exemplary process for enhancing image frames of a real-time video image stream by utilizing the sub-blocks and the clipping threshold level determined from a prior image frame. This exemplary process may greatly reduce the amount of iterations required for determining the sub-block matrices and/or clipping threshold levels for optimizing the image frames of a real-time video image stream. As such, the exemplary process of FIG. 3 may reduce delays in processing and displaying a real-time video image stream.

Still referring to FIG. 3, at step 302, the sub-block generation logic 105 may receive one or more input image frames (e.g., raw digital image frame) from the image sensor(s) 150. At step 304, the sub-block generation logic 105 may divide a current image frame based on a prior image frame's sub-block matrix (e.g., third sub-block matrix 218). That is, the sub-block generation logic 105 may start the sub-block size determination process for the current image frame with a predetermined sub-block size (e.g., third sub-block matrix 218) of the prior frame. At step 306, the sub-block generation logic 105 may determine whether the size of the prior image frame's sub-block matrix (e.g., third sub-block matrix 218) or another sub-block matrix generated by the sub-block generation logic 105 is suitable for enhancing the desired features of the current image frame. If the size of the sub-blocks of the prior image frame's sub-block matrix is not suitable, then, at step 305, the sub-block generation logic 105 may divide the current image into sub-blocks of a different size by performing additional iterations similarly to step 210 in FIG. 2. For example, the sub-block generation logic 105 may generate one or more sub-block matrices for the current image frame until a suitable size for enhancing the features of the current image frame is determined at step 306. At this step, since the sub-block generation logic 105 may have already performed multiple iterations for determining the third sub-block matrix 218, the processing time for determining the suitable size for the sub-block matrix of the current image frame may be significantly reduced.

Still referring to FIG. 3, upon determining the suitable size of the sub-block matrix of the current image frame is suitable at step 306, the histogram enhancement logic 106 may generate histograms for each sub-block (or region) of the sub-block matrix of the current image frame at step 308. For example, the histogram enhancement logic 106 may generate histograms by determining the Cumulative Distribution Function (CDF) corresponding to the sub-block matrix of the current image frame. At step 310, the histogram enhancement logic 106 may clip the histograms, in accordance with the process described for step 220 in FIG. 2, at a clipping threshold level determined based on a prior frame's clipping threshold level (e.g., third clipping threshold level 238). At step 312, the histogram enhancement logic 106 may determine whether the clipped histograms are suitable for enhancing the desired features of the current image frame. If the histograms clipped at the predetermined clipping threshold level (e.g., third clipping threshold level 238) is not suitable, then, at step 311, the histogram enhancement logic 106 may perform additional iterations similarly to step 230 in FIG. 2. For example, the histogram enhancement logic 106 may generate one or more different clipping threshold levels for the current image frame until a suitable clipping threshold level for enhancing the desired features of the current image frame is determined at step 312. At this step, since the histogram enhancement logic 106 may have already performed multiple iterations for determining the prior frame's clipping threshold level (e.g., third clipping threshold level 238), the processing time for determining the suitable clipping threshold level of the current image frame may be significantly reduced.

Still referring to FIG. 3, upon determining the suitable clipping threshold level at step 312, the mapping/interpolation logic 107 may map the pixel data obtained from the clipped histogram to generate an enhanced image frame for the current image frame at step 314. For example, the mapping/interpolation logic 107 may assign pixel intensity values obtained from the clipped CDF histogram to each pixel of the current image frame. The mapping/interpolation logic 107 may then apply one or more interpolation functions to the enhanced image frame generated based on the mapping process. In one embodiment, the mapping/interpolation logic 107 may interpolate one or more pixels of the enhanced image frame based on the location of each pixel in each sub-block of the enhanced image frame. At step 316, the mapping/interpolation logic 107 may output the interpolation applied enhanced image frame to the imaging logic 104 to generate an enhanced real-time image stream based on the enhanced image frame.

Figure 4:
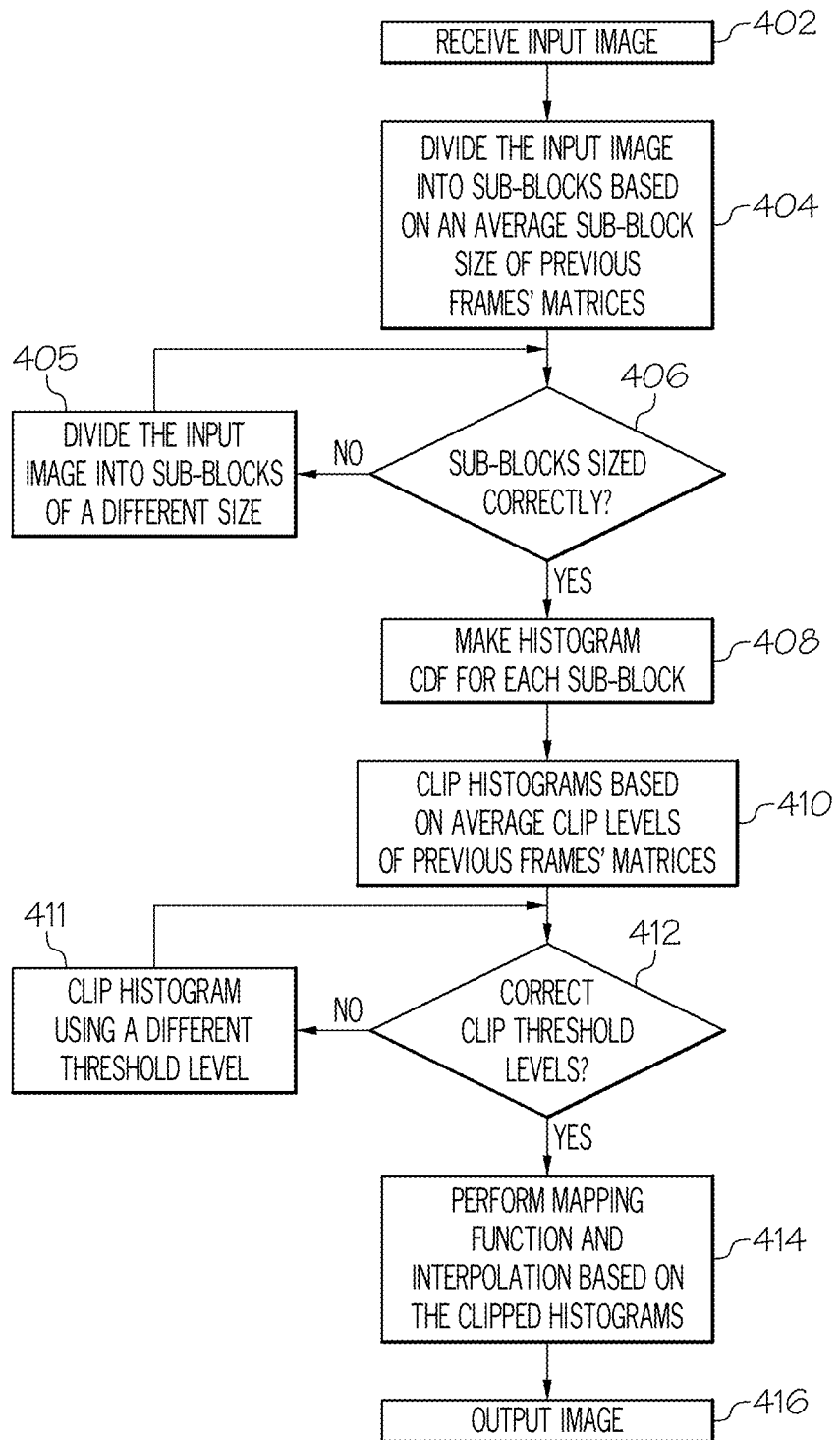
FIG. 4 illustrates another exemplary process of enhancing video images using the medical system of FIG. 1, according to aspects of this disclosure.

FIG. 4 shows another exemplary process for enhancing image frames of a real-time video image stream by utilizing the sub-blocks and the clipping threshold levels determined from multiple prior image frames. This exemplary process greatly reduces the amount of iterations that may be required for determining sub-block matrices and/or clipping threshold levels for optimizing the image frames of a real-time video image stream. As such, the exemplary process of FIG. 4 may reduce delays in processing and displaying a real-time video image stream. In addition, utilizing a moving average of the sub-block sizes and clipping threshold levels of multiple prior image frames may improve accuracy for enhancing video image streams that include spatial displacements (e.g., motion) of target features relative to a tip of the medical instrument 110.

In one embodiment, at step 402, the sub-block generation logic 105 may receive multiple input image frames from the image sensor 150. At step 404, the sub-block generation logic 105 may divide a current image frame by a sub-block matrix that is based on an average of sub-block matrices of multiple prior image frames. For example, the sub-block generation logic 105 may calculate the average size of the sub-block matrices of two, three, or more prior image frames. That is, the sub-block generation logic 105 may start the sub-block size determination process for the current image frame with a predetermined sub-block matrix based on multiple prior image frames. At step 406, the sub-block generation logic 105 may determine whether the size of the predetermined sub-block matrix generated by the sub-block generation logic 105 is suitable for enhancing the desired features of the current image frame. If the size of the sub-blocks of the predetermined sub-block matrix is not suitable, then, at step 405, the sub-block generation logic 105 may divide the current image frame into sub-blocks of a different size by performing additional iterations similarly to step 210 in FIG. 2. For example, the sub-block generation logic 105 may generate one or more sub-block matrices for the current image frame until a suitable size for enhancing the features of the current image frame is determined at step 406. At this step, since the sub-block generation logic 105 may have already performed multiple iterations for determining each sub-block matrix in the multiple prior frames, the processing time for determining the suitable size for the sub-block matrix of the current image frame may be significantly reduced.

Still referring to FIG. 4, upon determining the suitable size of the sub-block matrix of the current image frame is suitable at step 406, the histogram enhancement logic 106 may generate histograms for each sub-block (or region) of the sub-block matrix of the current image frame at step 408. For example, the histogram enhancement logic 106 may generate histograms by determining the CDF corresponding to the sub-block matrix of the current image frame. At step 410, the histogram enhancement logic 106 may clip the histograms, in accordance with the process described at step 220 in FIG. 2, at a predetermined clipping threshold level based on an average of multiple clipping threshold levels of multiple prior frames (e.g., two, three, or more multiple prior frames). At step 412, the histogram enhancement logic 106 may determine whether the histograms clipped at the predetermined clipping threshold level are suitable for enhancing the desired features of the current image frame. If the histograms clipped at the predetermined clipping threshold level is not suitable, then, at step 411, the histogram enhancement logic 106 may perform additional iterations similarly to step 230 in FIG. 2. For example, the histogram enhancement logic 106 may generate one or more different clipping threshold levels for the current image frame until a suitable clipping threshold level for enhancing the desired features of the current image frame is determined at step 412. At this step, since the histogram enhancement logic 106 may have already performed multiple iterations for determining the clipping threshold levels of multiple prior frames, the processing time for determining the suitable clipping threshold level of the current image frame may be significantly reduced.

Still referring to FIG. 4, upon determining the suitable clipping threshold level at step 412, the mapping/interpolation logic 107 may map the pixel data obtained from the clipped histogram to generate an enhanced image frame for the current image frame at step 414. For example, the mapping/interpolation logic 107 may assign pixel intensity values obtained from the clipped histogram to each pixel of the current image frame. The mapping/interpolation logic 107 may then apply one or more interpolation functions to the enhanced image frame generated based on the mapping process. In one embodiment, the mapping/interpolation logic 107 may interpolate one or more pixels of the enhanced image frame based on the location of each pixel in each sub-block of the enhanced image frame. At step 416, the mapping/interpolation logic 107 may output the interpolation applied enhanced image frame to the imaging logic 104 to generate an enhanced real-time image stream based on the enhanced image frame.

Figure 5:
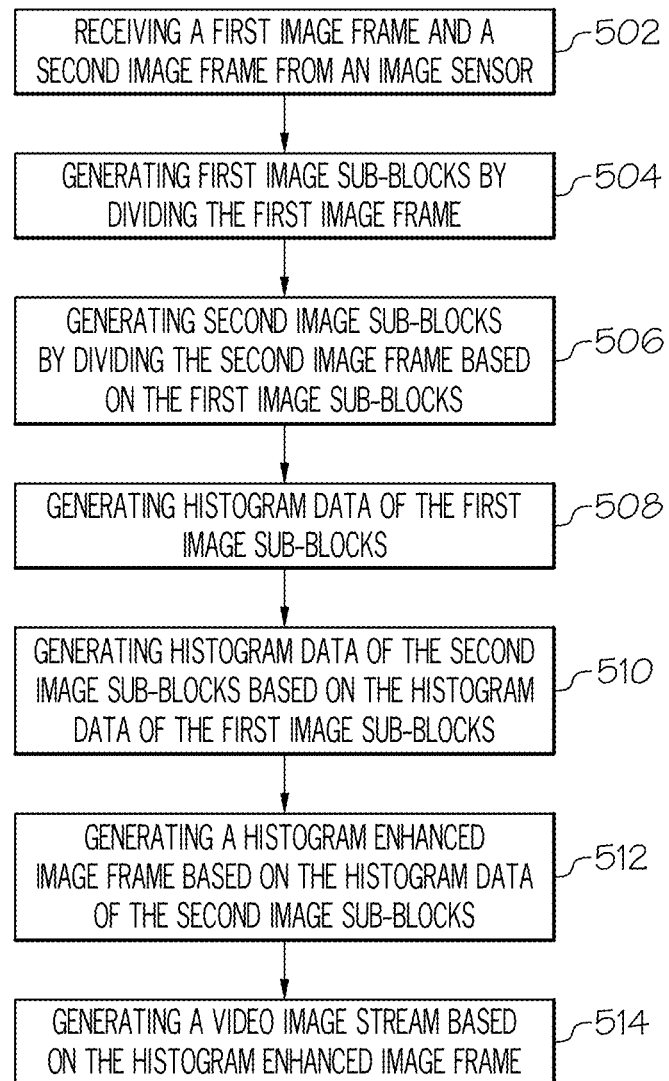
FIG. 5 illustrates a flow chart depicting an exemplary method of enhancing video images using the medical system of FIG. 1, according to aspects of this disclosure.

FIG. 5 shows a flow diagram of an exemplary method for enhancing image frames for a video image stream. At step 502, the sub-block generation logic 105 may receive a first image frame and a second image frame from the image sensor(s) 150. In one embodiment, the sub-block generation logic 105 may receive a plurality of image frames from the image sensor and generate sub-blocks in each of the plurality of image frames. The plurality of image frames may be at least three frames.

At step 504, the sub-block generation logic 105 may generate first image sub-blocks by dividing the first image frame. At step 506, the sub-block generation logic 105 may generate second image sub-blocks by dividing the second image frame based on the first image sub-blocks. In some embodiments, the sub-block generation logic 105 may perform one or more iterations of sizing each of the first image sub-blocks. That is, the sub-block generation logic 105 may determine a size of each of the first image sub-blocks based on the one or more iterations of the first image sub-blocks. Further, the sub-block generation logic 105 may determine a size of each of the second image sub-blocks based on one or more iterations of sizing each of the second image sub-blocks and/or a size of each of the first image sub-blocks.

At step 508, the histogram enhancement logic 106 may generate histogram data of the first image sub-blocks. In some embodiments, the histogram enhancement logic 106 may generate a histogram for each of the first image sub-blocks. Further, the histogram enhancement logic 106 may determine a clipping level of each histogram of the first image sub-blocks. Furthermore, the histogram enhancement logic 106 may determine the clipping level of each histogram of the first image sub-blocks based on one or more iterations of clipping each histogram of the first image sub-blocks. In another embodiment, the histogram enhancement logic 106 may generate a histogram for each sub-block of a plurality of prior image frames and determine a clipping level of each sub-block of the plurality of prior image frames based on an average histogram data of the plurality of prior image frames.

At step 510, the histogram enhancement logic 106 may generate histogram data of the second image sub-blocks based on the histogram data of the first image sub-blocks. In one some embodiments, the histogram enhancement logic 106 may generate the histogram data of the second image sub-blocks by generating a histogram for each of the second image sub-blocks. In one embodiment, the histogram enhancement logic 106 may generate the histogram for each of the second image sub-blocks at least based on a cumulative distribution function. Further, the histogram enhancement logic 106 may determine a clipping level of each histogram of the second image sub-blocks. Furthermore, the histogram enhancement logic 106 may determine the clipping level of each histogram of the second image sub-blocks based on one or more iterations of clipping each histogram of the second image sub-blocks and/or a clipping level of each histogram of the first image sub-blocks. In one embodiment, the histogram enhancement logic 106 may redistribute clipped data of each histogram of the second image sub-blocks into a bottom portion of the histogram for each of the second image sub-blocks. In another embodiment, the histogram enhancement logic 106 may determine the clipping level of each histogram of the second image sub-blocks based on one or more iterations of clipping each histogram of the second image sub-blocks and/or the average histogram data of a plurality of prior image frames.

At step 512, the histogram enhancement logic 106 may generate a histogram enhanced image frame based on the histogram data of the second image sub-blocks. In one embodiment, the histogram enhancement logic 106 may generate the histogram enhanced image by interpolating the histogram data of the second image sub-blocks. At step 514, the imaging logic 104 may generate a video image stream based on the histogram enhanced image frame.

Referring back to FIG. 1, which shows the display 109 of the medical system 100 communicatively coupled to the processor 102 of the image processing device 101, the processor 102 may be operable to transmit the enhanced image frames generated, in accordance with the processes and methods shown in FIGS. 2-5, to the display 109 for viewing by a user of the medical system 100. In some examples, the medical system 100 may be configured and operable to continuously execute the processes and methods shown in FIGS. 2-5 and described herein such that the display 109 may output an enhanced real-time video image stream to provide a continuous (e.g., live, real-time, etc.) images of the one or more target objects.

Each of the aforementioned systems, devices, assemblies, and methods may be used of enhance image frames to generate an enhanced real-time video image stream. By providing a medical device including an image processing system, a user may enhance a visualization of one or more features and/or characteristics of a target site within a subject during a procedure by generating an enhanced real-time video image stream using histogram enhanced data of one or more previous image frames. The medical device may allow a user to accurately identify a location of a target site, thereby reducing overall procedure time, increasing efficiency of procedures, and avoiding unnecessary harm to a subject's body caused by inaccurately locating target objects in the target treatment site.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

It should be appreciated that the image processing device 101 in FIG. 1 may be any computing device. The image processing device 101 also may include input and output ports to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of this disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of this disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical devices described herein may be using in combination with any other medical device known in the art, such as medical imaging systems or other scopes such as colonoscopes, bronchoscopes, ureteroscopes, duodenoscopes, etc., or other types of imagers.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method of enhancing video images in a medical device, the method comprising:
  receiving a first image frame and a second image frame from an image sensor;
  generating first image sub-blocks by dividing the first image frame;

generating second image sub-blocks by dividing the second image frame based on the first image sub-blocks;
generating histogram data of the first image sub-blocks;
generating histogram data of the second image sub-blocks based on the histogram data of the first image sub-blocks;
generating a histogram enhanced image frame based on the histogram data of the second image sub-blocks; and
generating a video image stream based on the histogram enhanced image frame.

2. The method of claim 1, further comprising:
performing one or more iterations of sizing each of the first image sub-blocks; and
determining a size of each of the first image sub-blocks based on the one or more iterations of the first image sub-blocks.

3. The method of claim 1, further comprising:
determining a size of each of the second image sub-blocks based on one or more iterations of sizing each of the second image sub-blocks and/or a size of each of the first image sub-blocks.

4. The method of claim 1, further comprising:
generating the histogram data of the first image sub-blocks by:
generating a histogram for each of the first image sub-blocks; and
determining a clipping level of each histogram of the first image sub-blocks.

5. The method of claim 4, wherein the clipping level of each histogram of the first image sub-blocks is determined based on one or more iterations of clipping each histogram of the first image sub-blocks.

6. The method of claim 1, further comprising:
generating the histogram data of the second image sub-blocks by:
generating a histogram for each of the second image sub-blocks; and
determining a clipping level of each histogram of the second image sub-blocks.

7. The method of claim 6, wherein the histogram for each of the second image sub-blocks is generated at least based on a cumulative distribution function.

8. The method of claim 6, wherein the clipping level of each histogram of the second image sub-blocks is determined based on one or more iterations of clipping each histogram of the second image sub-blocks and/or a clipping level of each histogram of the first image sub-blocks.

9. The method of claim 6, wherein generating the histogram data of the second image sub-blocks further comprises:
distributing clipped data of each histogram of the second image sub-blocks to the histogram for each of the second image sub-blocks.

10. The method of claim 1, wherein generating the histogram enhanced image frame comprises interpolating the histogram data of the second image sub-blocks.

11. The method of claim 1, further comprising:
receiving a plurality of image frames from the image sensor; and
generating sub-blocks in each of the plurality of image frames.

12. The method of claim 11, wherein the plurality of image frames is at least three frames.

13. The method of claim 11, further comprising:
generating a histogram for each sub-block of the plurality of image frames; and
determining a clipping level of each sub-block of the plurality of image frames based on an average histogram data of the plurality of image frames.

14. The method of claim 11, further comprising:
generating the histogram data of the second image sub-blocks by:
generating a histogram for each of the second image sub-blocks; and
determining a clipping level of each histogram of the second image sub-blocks.

15. The method of claim 14, wherein the clipping level of each histogram of the second image sub-blocks is determined based on one or more iterations of clipping each histogram of the second image sub-blocks and/or an average histogram data of the plurality of image frames.

16. A medical device, comprising:
a shaft;
an image sensor coupled to a distal end of the shaft;
at least one illumination device coupled to the distal end of the shaft;
one or more computer readable media storing instructions performing image processing to enhance video images; and
one or more processors configured to execute the instructions to perform the image processing comprising:
receiving a first image frame and a second image frame from the image sensor;
generating first image sub-blocks by dividing the first image frame;
generating second image sub-blocks of the second image frame based on the first image sub-blocks;
generating histogram data of the first image sub-blocks;
generating histogram data of the second image sub-blocks based on the histogram data of the first image sub-blocks;
generating a histogram enhanced image frame based on the histogram data of the second image sub-blocks; and
generating a video image stream based on the histogram enhanced image frame.

17. The medical device of claim 16, wherein generating the second image sub-blocks comprises:
determining a size of each of the second image sub-blocks based on one or more iterations of sizing each of the second image sub-blocks and/or a size of each of the first image sub-blocks.

18. The medical device of claim 16, wherein generating the histogram data of the second image sub-blocks comprises:
determining a clipping level of each histogram of the second image sub-blocks based on one or more iterations of clipping each histogram of the second image sub-blocks and/or a clipping level of each histogram of the first image sub-blocks.

19. The medical device of claim 16, wherein generating the histogram data of the second image sub-blocks comprises:
determining a clipping level of each histogram of the second image sub-blocks based on one or more iterations of clipping each histogram of the second image sub-blocks and/or an average histogram data of a plurality of image frames.

20. A non-transitory computer-readable medium storing instructions for enhancing video images, the instructions, when executed by one or more processors, causing the one or more processors to perform operations comprising:

receiving a first image frame and a second image frame from an image sensor;

generating first image sub-blocks by dividing the first image frame;

generating second image sub-blocks of the second image frame based on the first image sub-blocks;

generating histogram data of the first image sub-blocks;

generating histogram data of the second image sub-blocks based on the histogram data of the first image sub-blocks;

generating a histogram enhanced image frame based on the histogram data of the second image sub-blocks; and generating a video image stream based on the histogram enhanced image frame.

* * * * *